(12) United States Patent
Paranjape et al.

(10) Patent No.: US 8,895,340 B1
(45) Date of Patent: Nov. 25, 2014

(54) BIOSENSOR AND SYSTEM AND PROCESS FOR FORMING

(71) Applicant: Georgetown University, Washington, DC (US)

(72) Inventors: Makarand Paranjape, Silver Spring, MD (US); Yian Liu, Arlington, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/022,315

(22) Filed: Sep. 10, 2013

(51) Int. Cl.
*H01L 21/00* (2006.01)
*G01N 27/414* (2006.01)
*H01L 29/66* (2006.01)
*H01L 29/775* (2006.01)

(52) U.S. Cl.
CPC ...... *G01N 27/4146* (2013.01); *H01L 29/66439* (2013.01); *H01L 29/775* (2013.01); *Y10S 438/958* (2013.01)
USPC ............. 438/50; 438/674; 438/676; 438/712; 438/780; 438/958; 257/E21.536; 257/E21.585

(58) Field of Classification Search
None
See application file for complete search history.

(56) References Cited

U.S. PATENT DOCUMENTS

| | | | |
|---|---|---|---|
| 6,887,202 B2 | 5/2005 | Currie et al. | |
| 7,253,431 B2* | 8/2007 | Afzali-Ardakani et al. ..... | 257/20 |
| 7,276,389 B2* | 10/2007 | Kim et al. ........................ | 438/34 |
| 7,582,534 B2* | 9/2009 | Afzali-Ardakani et al. .. | 438/287 |
| 7,670,831 B2 | 3/2010 | Lee et al. | |
| 8,072,008 B2 | 12/2011 | Mukasa et al. | |
| 8,110,079 B2 | 2/2012 | Gooding et al. | |
| 8,338,296 B2* | 12/2012 | Sriraman et al. .............. | 438/674 |
| 8,642,432 B2* | 2/2014 | Afzali-Ardakani et al. .. | 438/289 |
| 8,748,242 B2* | 6/2014 | Daniel et al. .................. | 438/161 |
| 8,753,924 B2* | 6/2014 | Wainerdi et al. .............. | 438/122 |
| 2005/0126913 A1 | 6/2005 | Burke et al. | |
| 2005/0265914 A1 | 12/2005 | Gu et al. | |
| 2007/0114457 A1 | 5/2007 | Han et al. | |
| 2008/0035494 A1 | 2/2008 | Gomez et al. | |
| 2008/0093211 A1 | 4/2008 | Ramanath et al. | |
| 2009/0068241 A1 | 3/2009 | Britz et al. | |
| 2009/0212279 A1 | 8/2009 | Liu et al. | |
| 2010/0088040 A1 | 4/2010 | Johnson, Jr. | |

(Continued)

FOREIGN PATENT DOCUMENTS

WO    WO 2007/064355 A2    6/2007

OTHER PUBLICATIONS

International Search Report and Written Opinion for Application Serial No. PCT/US2010/060929, dated Feb. 24, 2011, 7 pp.

(Continued)

*Primary Examiner* — Zandra Smith
*Assistant Examiner* — Khanh Duong
(74) *Attorney, Agent, or Firm* — Dawn-Marie Bey; Bey & Cotropia PLLC

(57) ABSTRACT

A process for forming a carbon nanotube field effect transistor (CNTFET) device includes site-specific nanoparticle deposition on a CNTFET that has one or more carbon nanotubes, a source electrode, a drain electrode, and a sacrificial electrode on a substrate with an interposed dielectric layer. The process includes control of PMMA removal and electrodeposition in order to select nanoparticle size and deposition location down to singular nanoparticle deposition. The CNTFET device resulting in ultra-sensitivity for various biosensing applications, including detection of glucose at hypoglycemic levels.

23 Claims, 12 Drawing Sheets

(56) References Cited

U.S. PATENT DOCUMENTS

| | | |
|---|---|---|
| 2010/0239794 A1 | 9/2010 | Andrews et al. |
| 2010/0285514 A1 | 11/2010 | Claussen et al. |
| 2012/0153262 A1 | 6/2012 | Paranjape et al. |

OTHER PUBLICATIONS

Zhou, et al., "Novel In-Situ Decoration of Single-Walled Carbon Nanotube Transistors With Metal Nanoparticles," Jrnl. of Nanoscience and Nanotechnology, vol. 10, pp. 1-5, 2010.

Xiang, Yangchuan, "Synthesis and Electrochemical Characterization of Uniformly-Dispersed High Loading Pt Nanoparticles on Sonochemically-Treated Carbon Nanotubes," J. Phys. Chem. B, 108, pp. 19255-19259, 2004.

Girishkumar, G., "Carbon Nanostructures in Portable Fuel Cells: Single-Walled Carbon Nanotube Electrodes for Methanol Oxidation and Oxygen Reduction," J. Phys. Chem. B, 108, pp. 19960-19966, 2004.

Yao, Zhen, "High-Field Electrical Transport in Single-Wall Carbon Nanotubes," Physical Review Letters, vol. 84, No. 13, pp. 2941-2944, Mar. 27, 2000.

Gruner, G., "Carbon Nanotube Transistors for Biosensing Applications," Department of Physics, University of California Los Angeles, and Nanomix, Inc.

Allen, Brett Lee, "Carbon Nanotube Field-Effect-Transistor-Based Biosensors," Advanced Matreials, 19, pp. 1439-1451, 2007.

Balasubramaniam, Kannan, "Biosensors Based on Carbon Nanotubes," Anal Bioanal Chem., 385: 452-478, 2006.

Gruner, G., "Carbon Nanotube Transistors for Biosensing Applications," Anal. Bioanal. Chem., 384: 322-335, 2006.

Capek, Ignac, "Dispersions, Novel Nanomaterial Sensors and Nanoconjugates Based on Carbon Nanotubes," Advances in Colloid and Interface Science, 150, pp. 63-89, 2009.

Claussen, Jonathan C., et al., Electrochemical Biosensor of Nanotube-Augmented Carbon Nanotube Networks [online], ACS Nano, [retrieved on Jan. 25, 2009], Retrieved from the Internet: http://pubs.acs.org, 9 pp.

Cella, Lakshmi N., et al., "Single-Walled Carbon Nanotube-Based Chemiresistive Affinity Biosensors for Small Molecules: Ultrasensitive Glucose Detection," J. Am. Chem. Soc., JACS Communication, Jan. 19, 2010.

Day, Thomasm et al., "Electrochemical Templating of Metal Nanoparticles and Nanowires on Single-Walled Carbon Nanotube Networks," J. Am. Chem. Soc., 127, pp. 10639-10647, 2005.

Quinn, Bernadette M., "Electrodeposition of Noble Metal Nanoparticles on Carbon Nanotubes," J. Am. Chem. Soc., 127, pp. 6146-6147, 2005.

D. R. Kauffman and A. Star, "Chemically Induced Potential Barriers at the Carbon Nanotube-Metal Nanoparticle Interface," Nano Lett., vol. 7, No. 7, pp. 1863-1868, 2007.

A. Star, et al., "Label-Free Detection of DNA Hybridization Using Carbon Nanotube Network Field-Effect Transistors," Proc. Natl. Acad. Sci. USA, 103(4), pp. 921-926, Jan. 24, 2006.

T. Ozel, et al., "Polymer Electrolyte Gating of Carbon Nanotube Network Transistors," Nano Lett., vol. 5, No. 5, pp. 905-911, 2005.

K. J. Cash, et al., "Nanosensors and Nanomaterials for Monitoring Glucose in Diabetes," Trends in Molecular Medicine, vol. 16, Issue 12, pp. 584-593, Sep. 23, 2010.

J. Zhang, et al., "Mechanism of NO2 Detection in Carbon Nanotube Field Effect Transistor Chemical Sensors," Appl. Phys. Lett., 88(12), 3 pp., 2006.

J. Zhou, "Fabrication and Functionalization of Carbon Nanotube Field Effect Transistors for Bio-Sensing Applications," Graduate School of Arts and Sciences, Georgetown University, Dec. 17, 2009.

Chu, Haibin, et al., "Site-Specific Deposition of Gold Nanoparticles on SWNTs," J. Phys. Chem. C, 112, pp. 13437-13441, 2008.

Gao, Ruifang, et al., "Amine-Terminated Ionic Liquid Functionalized Carbon Nanotube-Gold Nanoparticles for Investigating the Direct Electron Transfer of Glucose Oxidase," Electrochemistry Communications 11, pp. 608-611 (2009).

Lee, Chung-Hun, et al., "Comparison of Amperometric Biosensors Fabricated by Palladium Sputtering, Palladium Electrodeposition and Nafion/Carbon Nanotube Casting on Screen-Printed Carbon Electrodes," Biosensors and Bioelectronics 22, pp. 877-884 (2007).

A. Star, J. Phys. Chem. B, 2006, 110, 21014-21010.

International Search Report and Written Opinion for Application No. PCT/US14/41501, dated Oct. 6, 2014, 8 pp.

* cited by examiner

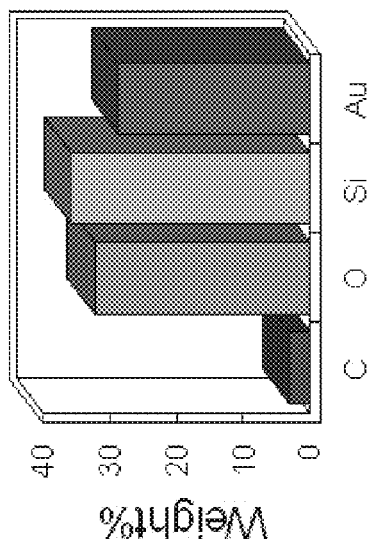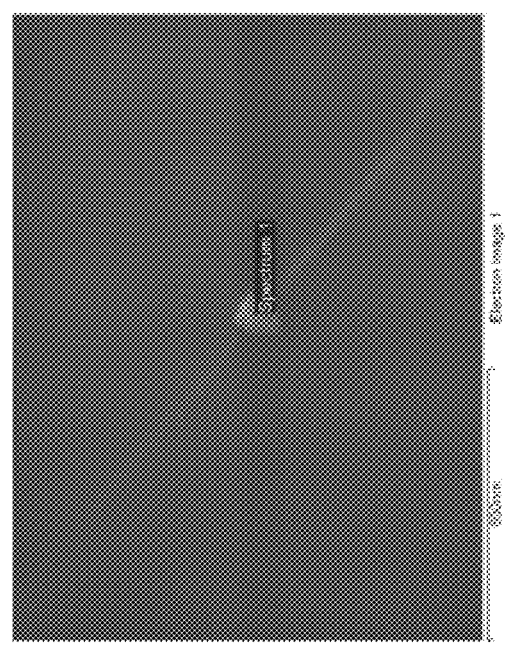
Figure 10a
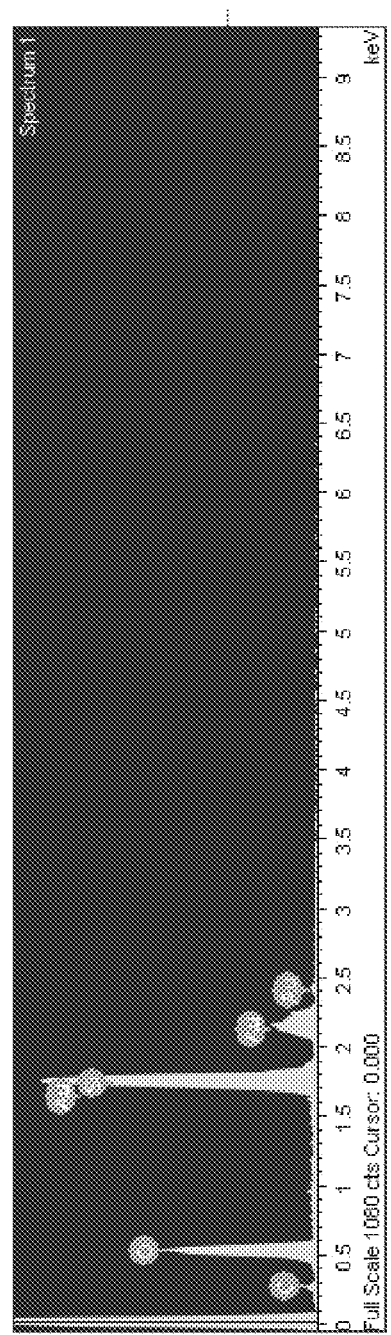
Figure 10b

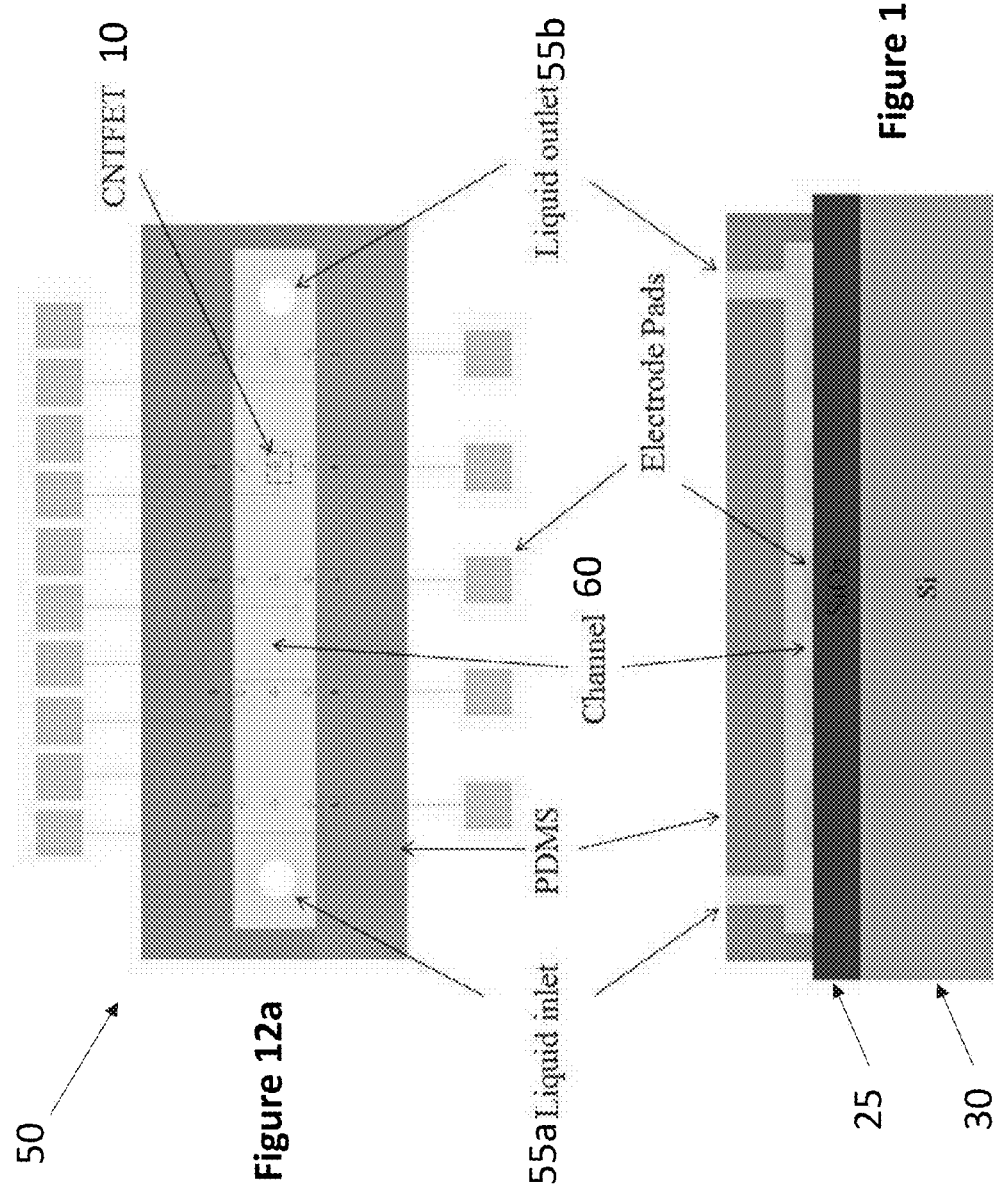

BIOSENSOR AND SYSTEM AND PROCESS FOR FORMING

CROSS-REFERENCE TO RELATED APPLICATIONS

The following commonly owned application is incorporated herein by reference in its entirety: U.S. application Ser. No. 12/970,997 for System and Process for Forming Carbon Nanotube Sensors filed Dec. 17, 2010.

BACKGROUND

1. Technical Field of the Embodiments

The embodiments are generally directed to the field of bio-sensing and the processes for forming bio-sensors.

2. Description of the Related Art

Currently available glucose sensor technology is limited in its efficacy for sensing low glucose concentration in individuals, also called hypoglycemia. Hypoglycemia is a common complication of diabetes and it is very dangerous to people with diabetes especially for new born babies. Hypoglycemia occurs when the glucose concentration in the blood is low and leads to insufficient supply of glucose to the brain. This condition leads to numerous problems ranging from dysphoria to seizures, unconsciousness, and permanent brain damage. The condition may even result in death. Currently, the detection of hypoglycemia is still a challenge for glucose sensors on the market. Current sensors either cannot accurately detect low glucose concentration or there is lag during detection.

The embodiments described herein are directed to a glucose sensor based on carbon nanotube field effect transistor (CNTFET) technology, wherein the process for forming is novel process and includes the controlled deposition of gold (Au) nanoparticles on the carbon nanotubes. Carbon nanotubes and Au nanoparticles possess outstanding electrical and biological properties that make them ideal materials for bio-sensing applications. Through the controlled deposition of Au nanoparticles onto carbon nanotube, the sensitivity of the glucose sensor can be tuned in order to achieve high sensitivity and therefore realizing the detection of hypoglycemia.

Current site-specific Au nanoparticle deposition method involves electrochemical dip-pen nanolithography as described in Chu et al., J. Phys. Chem. 2008, 112, 13437-13441. This method uses atomic force microscopy (AFM) to achieve site specific deposition. As shown in prior art FIG. 1, the tip of the AFM dip-pen is first immersed in a gold chloride solution, and then a voltage is applied to the tip. As the tip sweeps over the carbon nanotube, Au nanoparticles can be deposited onto the carbon nanotube through electrochemical reaction. The result of an exemplary deposition sweep is shown in FIGS. 2a and 2b. The AFM deposition process does not provide for adequate Au location, size or number control to achieve the glucose sensor efficacy required for sensing hypoglycemia.

More particularly, in the AFM deposition process, the locations of the deposition sites are controlled by the location of the AFM tip. Since there is gold chloride solution on the AFM tip, the tip has to be brought to the selected location before starting to sweep across the carbon nanotube, and the location of the tip cannot be controlled precisely. The present embodiments described herein solve this problem by using an electron beam to control the locations of the deposition sites which can easily achieve nanometer scale precision.

Further, in the AFM deposition process, the number of the Au nanoparticles cannot be controlled due to the geometry of the AFM tip. The present embodiments described herein solve this problem since individual Au nanoparticles can be deposited one at a time.

Finally, the AFM deposition process is relatively inefficient. The present embodiments described herein use e-beam lithography to create the deposition sites, which allows for particularity in the deposition patterns. For example, and as described in detailed below, the size of the PMMA opening may be controlled to achieve single Au nanoparticle deposition or multiple Au nanoparticle deposition on a carbon nanotube. Additionally, the present embodiments allow for the creation of multiple PMMA openings at a time, and deposition of Au nanoparticle(s) onto these multiple individual sites at the same time. The AFM deposition process only allows for deposition of the Au nanoparticles onto one site each time since the deposition occurs only when the AFM tip touches the carbon nanotube.

These and other advantages over the prior art sensors and processes are described herein with respect to the present embodiments directed to a novel method to realize in-situ site specific deposition of gold (Au) nanoparticles on single-walled carbon nanotube field effect transistors (CNTFETs) for ultra-sensitive bio-sensing applications, including glucose sensing.

BRIEF DESCRIPTION OF THE FIGURES

The following figures exemplify the embodiments described herein and are intended to be reviewed in combination with the detailed descriptions provided below.

FIGS. 10(a) and 10(b) are (a) EDX image of the single Au nanoparticle and (b) graphical representation of the materials, including Au nanoparticle, imaged in (a), in accordance with embodiments described herein;

FIGS. 12(a) and 12(b) are (a) a schematic top view of PDMS channel and (b) side view of PDMS channel device configuration.

SUMMARY OF THE EMBODIMENTS

Figure 1:
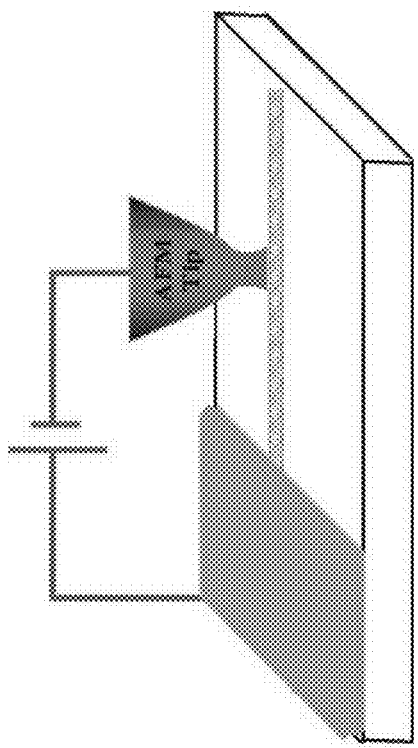
FIG. 1 is a schematic representation of an existing process for depositing nanoparticles using an atomic force microscopy (AFM) deposition process.
Figure 2A:
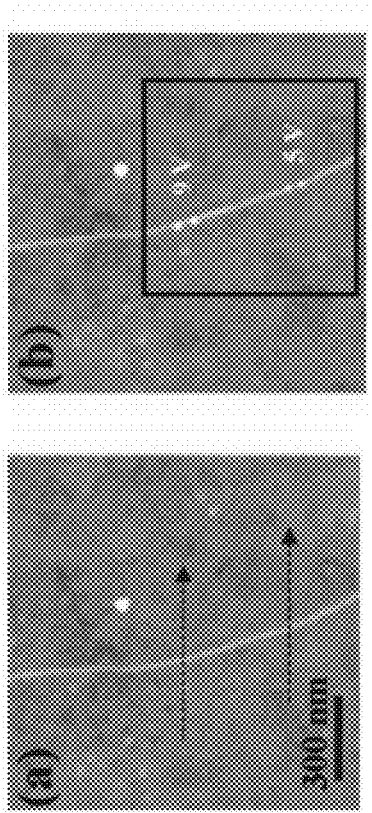
FIGS. 2(a) and 2(b) are AFM images showing exemplary typical Au deposition results using the existing AFM process of FIG. 1.
Figure 2B:
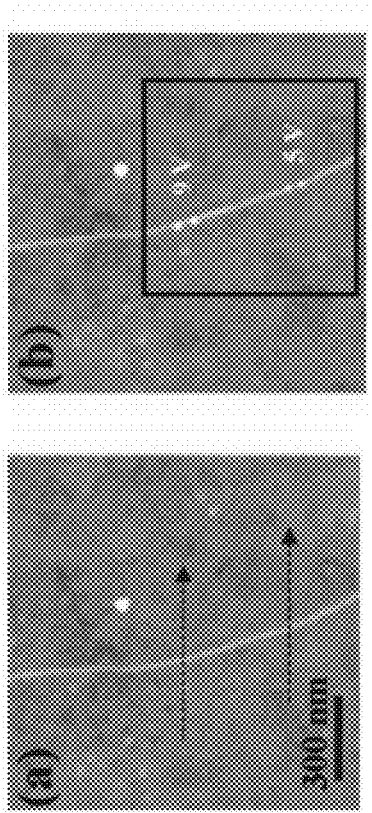

A first embodiment described herein includes a process for forming a functionalized carbon nanotube field effect transistor (CNTFET) device including site-specific nanoparticle deposition on a carbon nanotube field effect transistor (CNTFET) including one or more carbon nanotubes, a source electrode, a drain electrode, and a sacrificial electrode on a substrate with an interposed dielectric layer. The process comprises: passivating the CNTFET with a layer of Poly (methyl methacrylate) (PMMA); programming a processor of an electron-beam lithography system with a predetermined removal pattern; applying electron-beam lithography using the electron-beam lithography system to the CNTFET to remove portions of the PMMA layer and expose one or more underlying portions of the one or more carbon nanotubes and the sacrificial electrode of the CNTFET in accordance with the programmed predetermined removal pattern; applying an amount of an electrolyte solution to the CNTFET, including the exposed one or more underlying portions of the one or more carbon nanotubes and the sacrificial electrode; applying a voltage to the sacrificial electrode while grounding the source and drain electrodes; and electrodepositing one or more nanoparticles formed from atoms of the sacrificial electrode onto the one or more exposed portions of the one or more carbon nanotubes.

A second embodiment described herein includes a process for forming a functionalized carbon nanotube field effect transistor (CNTFET) device including site-specific nanoparticle deposition on a carbon nanotube field effect transistor (CNTFET) including one or more carbon nanotubes, a source electrode, a drain electrode, and a sacrificial electrode on a substrate with an interposed dielectric layer. The process comprises: removing portions of a protective layer covering the one or more carbon nanotubes in accordance with a predetermined removal pattern to expose one or more individual underlying portions of the one or more carbon nanotubes and to expose the sacrificial electrode of the CNTFET, wherein each of the exposed one or more individual underlying portions of the one or more carbon nanotubes has a first predetermined dimension; applying an amount of an electrolyte solution to the CNTFET, including the exposed one or more underlying portions of the one or more carbon nanotubes and the sacrificial electrode; applying a voltage to the sacrificial electrode while grounding the source and drain electrodes; and electrodepositing one or more nanoparticles each having a predetermined second dimension formed from atoms of the sacrificial electrode onto the one or more exposed portions of the one or more carbon nanotubes, wherein the first predetermined dimension is only slightly larger than the second predetermined dimension.

In a third embodiment, a microfluidic device for assessing the contents of fluid introduced thereto includes: at least one microfluidic channel having multiple functionalized carbon nanotube field effect transistors (CNTFET) formed in accordance with the process of the first embodiment and including one or more carbon nanotubes, a source electrode, and a drain electrode formed on a substrate with an interposed dielectric layer; a single access point formed in the microfluidic device for introducing the fluid to the at least one microfluidic channel; and a single exit point formed in the microfluidic device for removing the fluid from the least one microfluidic channel.

In a fourth embodiment, a process for forming a functionalized carbon nanotube field effect transistor (CNTFET) device including site-specific nanoparticle deposition on a carbon nanotube field effect transistor (CNTFET) including one or more carbon nanotubes, a source electrode, a drain electrode, and at least a first and second sacrificial electrode on a substrate with an interposed dielectric layer, includes: removing portions of a protective layer covering the one or more carbon nanotubes in accordance with a first predetermined removal pattern to selectively expose a first individual underlying portion of the one or more carbon nanotubes and to selectively expose the first sacrificial electrode of the CNTFET; applying an amount of an electrolyte solution to the CNTFET, including the exposed first underlying portion and the exposed first sacrificial electrode; applying a first voltage to the first sacrificial electrode while grounding the source and drain electrodes; electrodepositing one or more nanoparticles formed from first atoms of the first sacrificial electrode onto the first exposed underlying portions of the one or more carbon nanotubes; removing portions of a protective layer covering the one or more carbon nanotubes in accordance with a second predetermined removal pattern to selectively expose a second individual underlying portion of the one or more carbon nanotubes and to selectively expose the second sacrificial electrode of the CNTFET; applying an amount of an electrolyte solution to the CNTFET, including the exposed second underlying portion and the exposed second sacrificial electrode; applying a second voltage to the second sacrificial electrode while grounding the source and drain electrodes; and electrodepositing one or more nanoparticles formed from second atoms of the second sacrificial electrode onto the second exposed underlying portions of the one or more carbon nanotubes.

DETAILED DESCRIPTION OF THE EMBODIMENTS

A carbon nanotube field effect transistor uses either a single carbon nanotube or a network of carbon nanotubes as the channel material. Similar to traditional field effect transistors, a carbon nanotube field effect transistor uses an electric field to control and modulate the electric current. CNTFETs can be used as nano-sensors. Adsorption of molecules onto the carbon nanotube surface can cause depletion or accumulation of charges. Therefore, detection can be observed as a change in conductance between source and drain electrodes. CNTFETs have many advantages as biosensors. First, because of their semiconducting nature, CNTFETs can easily transduce the interaction between the nanotube and molecules into an amplified electronic signal. Second, carbon nanotubes are comparable in size to biological molecules, ensuring appropriate size compatibility between the detector and the detected species. In addition, all carbon atoms are on the surface of the CNT, which facilitates direct contact and interaction with the molecules in the environment to which it is exposed. These features, together with its 1-D structure makes the conductance of the CNTFET very sensitive to the local environment. Any local disturbance could dramatically change the carrier concentration along the carbon nanotube, resulting in fast detection and high sensitivity.

With respect to the embodiments described herein, carbon nanotube field effect transistors ("CNTFETs") may be decorated with nanoparticles as further described to facilitate the binding of chemical/biological molecules of interest thereto. CNTFETs generally includes one or more CNTs, one or more electrodes contacting the two ends of the nanotube(s), an insulating dielectric layer (e.g., $SiO_2$) on top of or underneath the nanotube(s), and a conductive gate (e.g., doped silicon (if underneath of the nanotube), or a metallic top-gate (if on top of the nanotube) within a few hundred nanometers to the nanotube but insulated by the dielectric layer. Various techniques are used to develop CNTs including discharge, laser ablation and chemical vapor deposition ("CVD") and such techniques are well known to those skilled in the art. The electrodes may be patterned using photolithography or electrode beam lithography. Further, the electrodes may be metallic or non-metallic (e.g., conductive polymers, indium-tin-oxide (ITO) and the like).

An Au nanoparticle is a nano material that has been used to enhance the electron transfer between enzyme and electrodes. As described herein, the Au nanoparticles are used to 'shuttle' electrons from the oxidation-reduction (redox) active center of glucose oxidase (GOx) to the electrodes. Glucose oxidase is an enzyme that catalyzes the oxidation of glucose to D-gluconolactone. The key component of GOx is the redox center, flavin adenine dinucleotide (FAD). On interaction with glucose, FAD is reduced to $FADH_2$ (hydroquinone form), by accepting two hydrogen atoms (a net gain of two electrons), whereas glucose loses two hydrogen atoms and forms the redox product of gluconolactone. By placing an Au nanoparticle between GOx and a carbon nanotube, the generated electrons can be transferred from the redox center to the carbon nanotube through the Au nanoparticle, generating electronic signals. Au nanoparticles can shuttle electrons between GOx and nanotubes due to the following reasons. First, the large specific surface area of the small Au nanoparticles greatly enhances the enzyme absorption ability. Second, GOx molecule is formed with a hydrophilic FAD in the core of the molecule and a hydrophobic shell out side. This shell is flexible and deformable. During the adsorption onto the Au nanoparticle, the amphiphilic GOx molecule deforms and attaches to the hydrophilic Au nanoparticle surface by its hydrophilic FAD, shortening the distance between FAD and Au nanoparticles.

Figure 3:
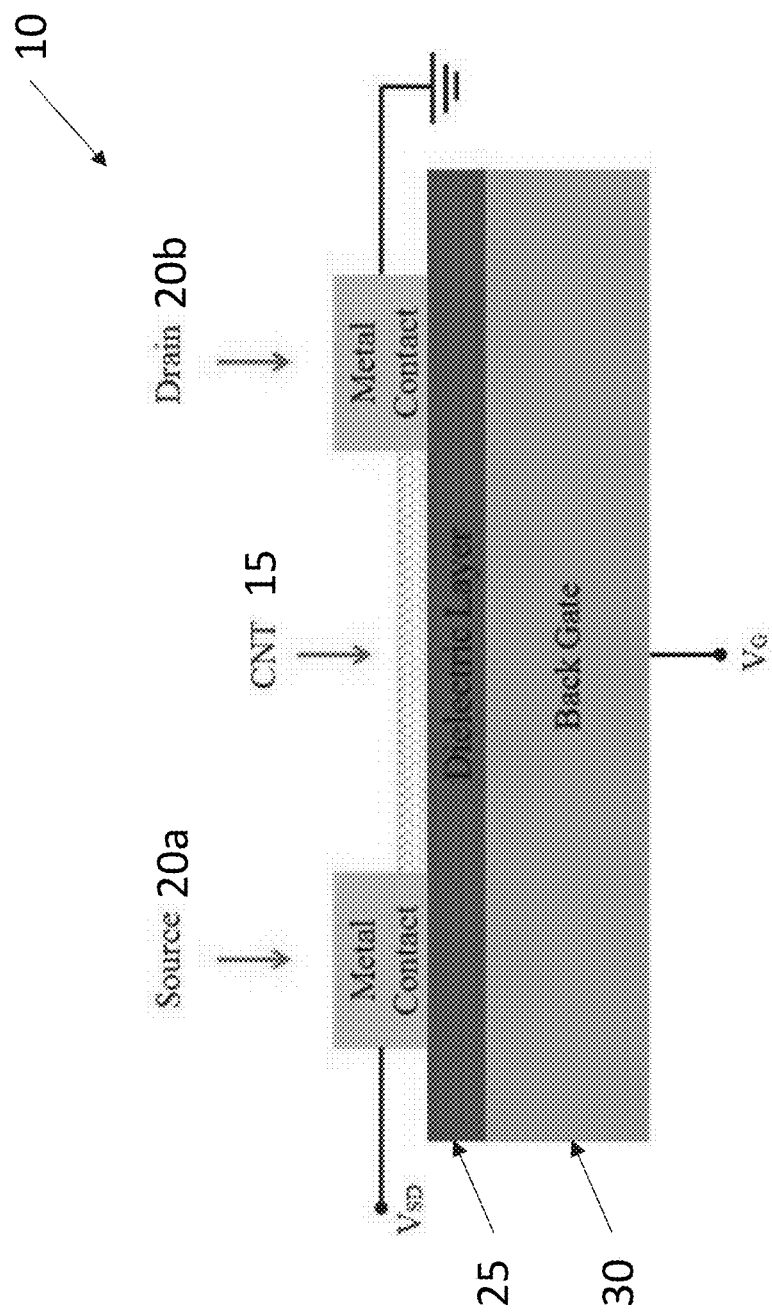
FIG. 3 is schematic side view diagram of a CNTFET in accordance with embodiments described herein.
Figure 4:
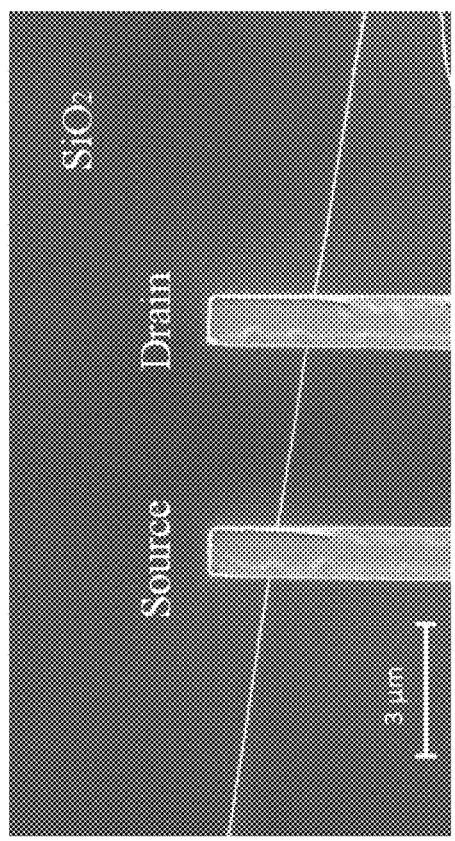
FIG. 4 is an SEM image of a CNTFET in accordance with embodiments described herein.

Referring to FIG. 3, in the present embodiments, the CNT-FET devices 10 consist of one or more carbon nanotubes (CNTs) 15, first and second metallic electrodes 20a, 20b contacting the (CNTs) 15, serving as source 20a and drain 20b, an insulating dielectric layer (e.g., $SiO_2$) 25 underneath the CNTs, and a conductive "back" gate (e.g., Si) 30 within a few hundred nanometers to the CNTs 15 but insulated by the dielectric layer 25. The conductivity of the CNT(s) between the source 20a and drain 20b electrodes can be modulated by a voltage ($V_G$) applied to the gate. The SEM image in FIG. 4 shows a top view of an exemplary CNTs 15 with first and second metallic electrodes 20a, 20b configuration in accordance with the embodiments described herein. A Cr/Au metal bilayer is deposited onto the CNTs 15 using electron-beam lithography and sputtering to make source and drain electrodes 20a, 20b. One skilled in the art recognizes that CNT-FETs may be formed using multiple CNTs, including CNT films or networks, including multiple CNTs, as described in the teachings of A. Star, E. Tu, J. Niemann, J-C. P. Gabriel, C. S. Joiner, and C. Valcke, Proc Natl Acad Sci USA. 2006 Jan. 24; 103(4): 921-926 and T. Ozel, A. Gaur, J. A. Rogers, and M. Shim, Nano Lett., 2005, 5 (5), pp 905-911 which are incorporated herein by reference.

Figure 5:
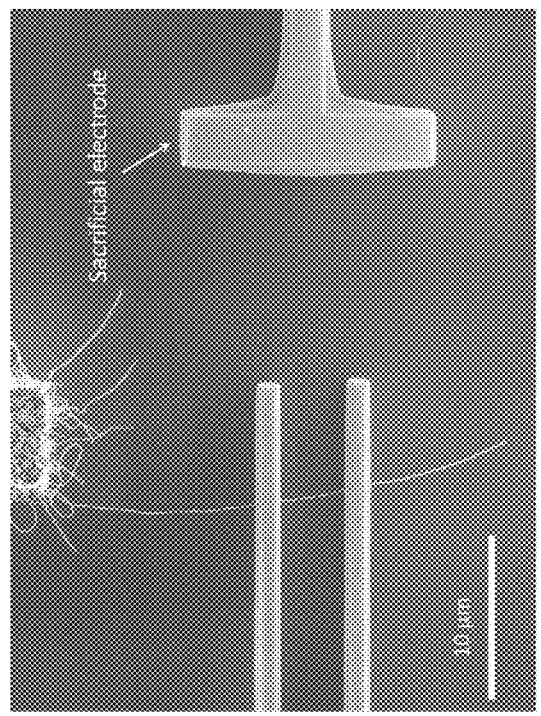
FIG. 5 is an SEM image of a pre-Au deposition CNTFET device configuration with a sacrificial Au electrode in accordance with embodiments described herein.

Referring to the SEM image of FIG. 5, a sacrificial electrode 35 is also included on the device 10 to serve as a source of Au. In a particular example, the sacrificial electrode 35 is composed of a bilayer of metals Cr/Au (Cr used as an adhesion layer for Au—could also use other adhesion layers, e.g. Ti, Titanium), at approximately 25 Å and 800 Å, respectively, and is located approximately 5-20 μm from the contact electrodes and is approximately 4 μm wide. Site-specific Au nanoparticles deposition is achieved through electrodeposition with the help of a Poly(methyl methacrylate) (PMMA) layer. In accordance with embodiments described herein, the substrate is first passivated by a layer of PMMA. The thickness of this layer is about 180 nm. Next, e-beam lithography is used to create a small opening in the PMMA, leaving the site open for decoration and the sacrificial electrode exposed. Referring the schematic of FIG. 6, a drop of electrolyte Phosphate Buffered Saline (PBS) 40 is applied to the device 10 and a positive voltage ($V_{SE}$) is applied to the sacrificial electrode 35, with both source and drain electrodes 20a, 20b grounded. Au atoms from the sacrificial electrode 35 are oxidized by the positive voltage ($V_{SE}$) and dissolved in the PBS as Au ions, and subsequently reduced at the exposed CNT side walls as Au nanoparticles. By adjusting the number and sizes of the deposition sites created in the PMMA, a certain number or a near continuous coating of Au nanoparticles can be controllably deposited on the CNTs 15. In an alternative embodiment, Au nanoparticles can be deposited onto multiple designated sites at the same time by creating multiple PMMA openings at once. The Au nanoparticle size can vary from 10 nm to over 100 nm, depending on the voltage applied to the sacrificial electrode 35 and the deposition time. For enzymatic reactions such as glucose detection using GOx that involves electron transfer through the Au nanoparticles, the ideal size of Au nanoparticles ranges from 10 nm to 30 nm to ensure that the reaction center of the GOx and the CNT are in close proximity. If the Au nanoparticles are only used as anchoring sites in non-enzymatic reactions, the size of the Au nanoparticles is not as critical. Finally, a SU-8 passivation layer is deposited onto the electrodes 20a, 20b to ensure proper functioning of the device in aqueous environment.

Figure 7A:
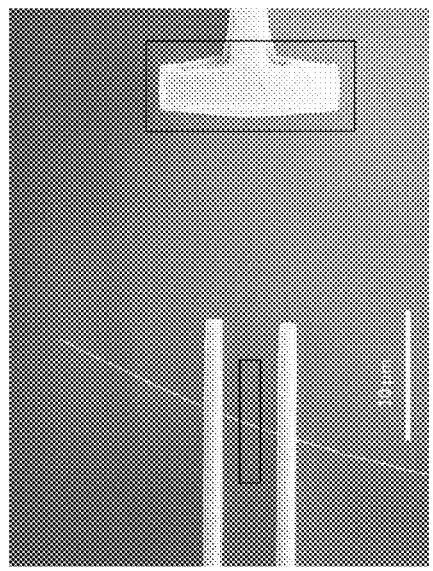
FIGS. 7(a)-7(c) are SEM images showing (a) CNTFET with sacrificial electrode with indication of PMMA windows to be opened by e-beam lithography, (b) indication of PMMA window opened by e-beam lithography, and (c) Au nanoparticles deposited only at designed site in the PMMA in accordance with embodiments described herein.
Figure 7B:
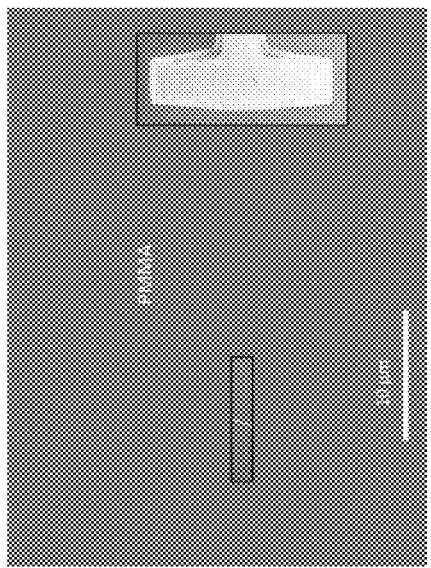
Figure 7C:
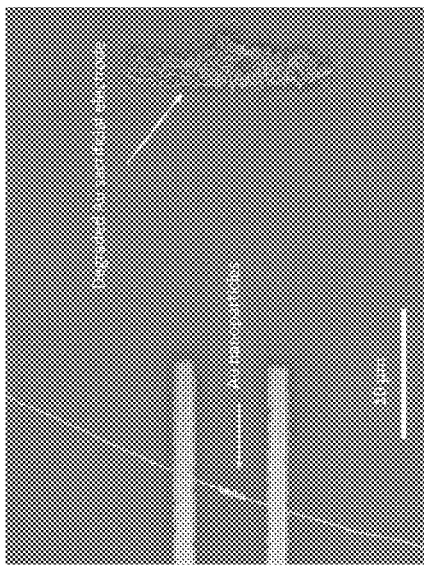

FIGS. 7a-7c provide a series of SEM images illustrating dimensions and various stages of the Au deposition process described above. FIG. 7a shows the device configuration prior to PMMA passivation. FIG. 7b shows the device configuration post-PMMA passivation. FIG. 7c shows the device configuration after the steps of e-beam lithography to create the desired opening(s) pattern in the PMMA, sacrificing of the sacrificial electrode to deposit Au in the openings and onto the CNT and removal of the remaining PMMA from the device.

Figure 8B:
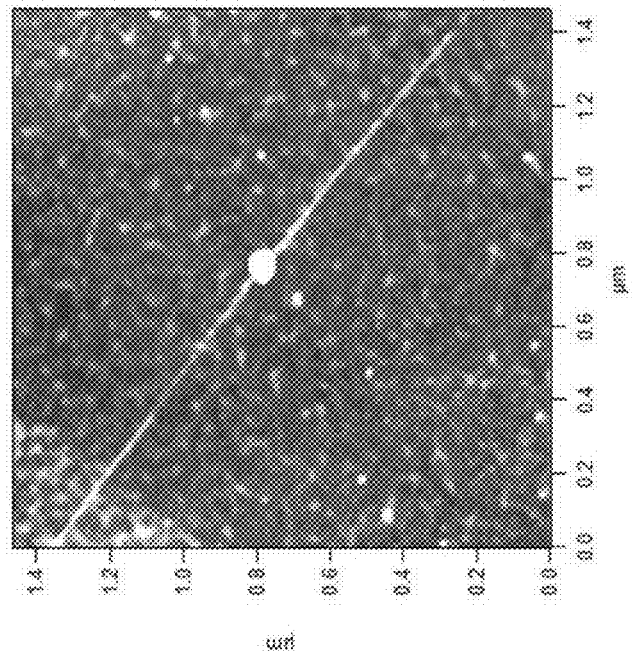
FIGS. 8(a) and 8(b) are (a) SEM images showing one single Au nanoparticle is deposited onto selected site and (b) an AFM image of the single Au nanoparticle in accordance with embodiments described herein.
Figure 8A:
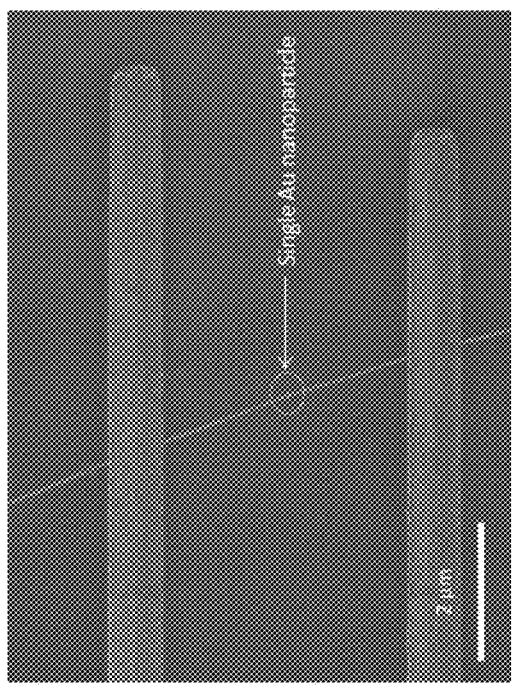
Figure 9A:
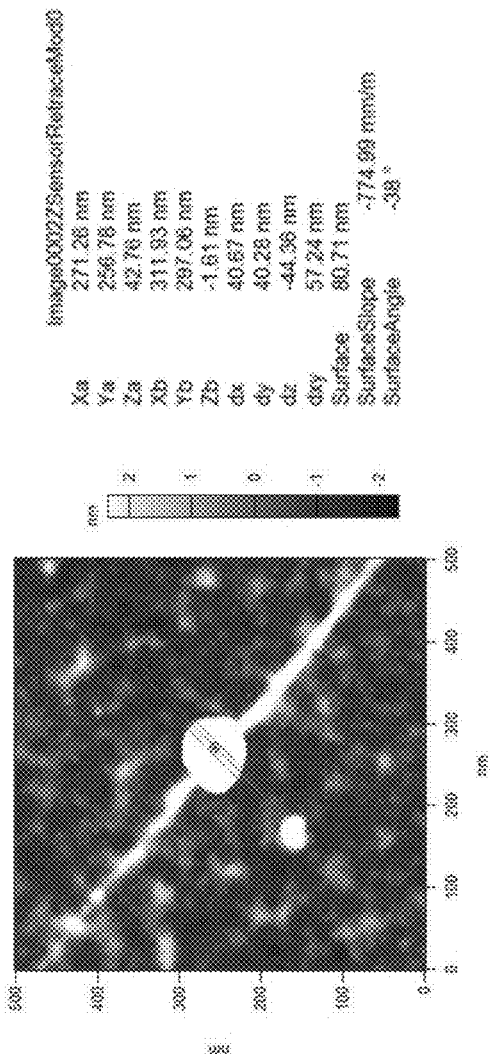
FIGS. 9(a) and 9(b) are (a) an AFM image of the single Au nanoparticle and (b) a graphical representation of the measured size of the Au nanoparticle in accordance with embodiments described herein.
Figure 9B:
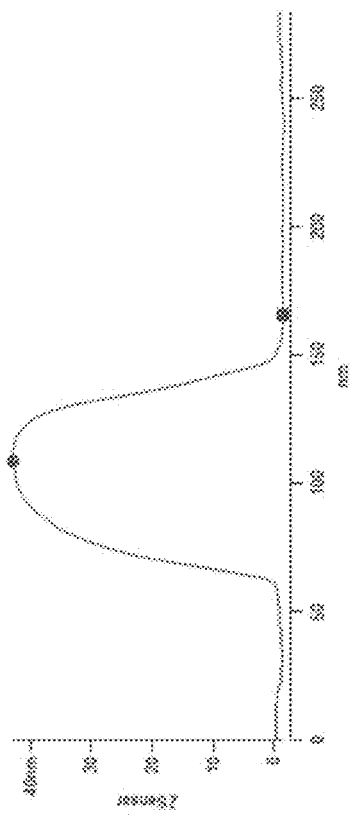

FIGS. 8a, 8b and 9a show various images of a single Au nanoparticle deposited on a CNT in accordance with the process described in the embodiments herein. FIG. 9b provides an indication of approximate size of the single Au nanoparticle, e.g., 40 nm, in graphical form. Similarly, FIGS. 10a and 10b provide for additional confirmation of Au single nanoparticle deposition on the CNT and size thereof using Energy Dispersive X-Ray Analysis (EDX or EDA). EDX provides elemental identification and quantitative compositional information. As illustrated in FIG. 10b, the EDX analysis of the CNT with Au nanoparticle shown in FIG. 10a shows elements C, O, Si and Au as expected.

Figure 11B:
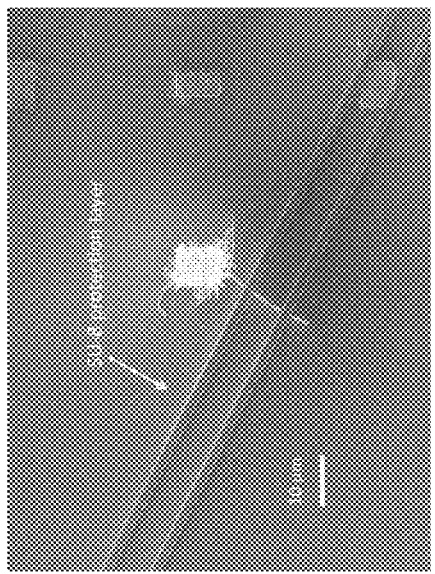
FIGS. 11(a) and 11(b) are (a) an SEM image of a CNTFET device (b) an SEM image of (a) with SU-8 protection layer in accordance with embodiments described herein.
Figure 11A:
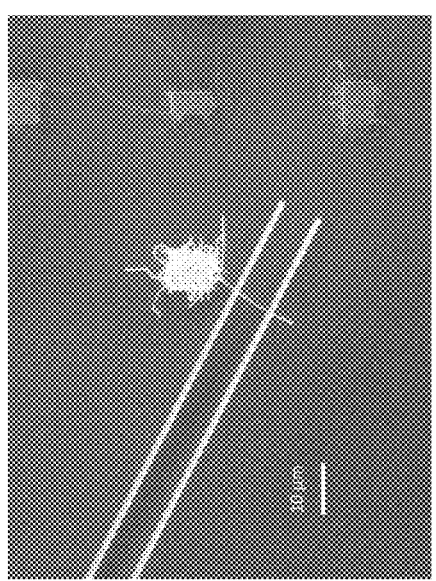

FIGS. 11a and 11b are SEM images showing the device 10 before and after the protective coating, e.g., SU-8, is applied thereto.

In a specific, non-limiting example an Au nanoparticle deposition process in accordance with the description provided herein includes design of the preferred deposition pattern using one or more computer programs compatible with the lithographic system to be used for e-beam lithography. An exemplary computer program includes Design CAD 2000. Prior to writing the deposition pattern on the device, a coating of PMMA 950 C2 is applied to the sample at a spin rate of 4000 rpm. The sample is heated on a hotplate at 180° C. for 2 minutes. Via e-beam lithography, the designed deposition pattern is applied to the PMMA layer. The electron beam having the following characteristics: Aperture size is 30 µm; Voltage is 30 kV; Dosage is 350 µC/cm$^2$. The PMMA is developed in Methyl isobutyl ketone (MIBK) for 60 seconds. Next, the sample is rinsed with IPA and dried with $N_2$. Approximately 10 µl of PBS is applied onto the sample. The source and drain electrodes are ground and a positive voltage is applied to the sacrificial electrode. The applied voltage on the sacrificial electrode is swept from 0.5 V to 1.5 V. The voltage and the number of the sweep cycles may be adjusted according to the desired number and size of the Au nanoparticles. The sample is rinsed with DI water and dried with $N_2$. Finally, the PMMA layer is removed by immersing the sample in acetone.

Further, glucose oxidase molecules (GOx) are bound onto the Au nanoparticles using thiol linking molecules. The strong covalent bond between the gold and thiol groups on biomolecules provides a more robust bond compared to non-specific adsorption of biomolecules onto the CNT sidewalls, thus enabling the use of thiol linking molecule to specifically immobilize GOx to the Au nanoparticles. In addition, the catalytic nature and suitability for binding to the thiol as well as the excellent conductivity of the metallic Au nanoparticles makes the delivery of the chemical event at the biomolecule to the CNT channel much easier. After this step, the detection of glucose can be conducted for a variety of glucose solution concentrations. Negative and positive control solutions will also be used to investigate the response due to interferents. Additional aspects of the present embodiments are described in U.S. application Ser. No. 12/970,997 for System and Process for Forming Carbon Nanotube Sensors, the substance of which is incorporated herein by reference in its entirety.

Calibration of the CNTFET devices 10 may be achieved using a device such as that shown in FIGS. 12*a* and 12*b* (top and side views) which includes a Polydimethylsiloxane (PDMS) microfluidic system 50 for the delivery of glucose solution to one or more devices 10. Referring to FIG. 12*a*, multiple CNTFET devices 10 are included in a single PDMS microfluidic system 50. In addition to the CNTFET devices 10, the PDMS microfluidic system 50 includes at least one liquid inlet 55*a* and at least one liquid outlet 55*b* connected to a microfluidic channel 60 that lies above the CNTFET devices 10. In operation, glucose solution is injected from the liquid inlet 55*a* and flows along the microfluidic channel 60 so that glucose solution flows over and interacts with multiple CNTFET devices 10. Glucose solution exits the channel through the liquid outlet 55*b*. By way of example, syringes with luer lock fittings may be used to deliver the solution to the liquid inlet 55*a*. Through modification of the concentration of glucose solution that is introduced to the system 50 and monitoring of the response of CNTFET devices 10, the CNTFET devices 10 may be calibrated in accordance with intended application.

In an alternative use of the configuration shown in FIGS. 12*a* and 12*b*, the microfluidic system 50 could be used to assess the contents of fluids injected therein. Such fluids could include bodily fluids, e.g., blood, interstitial fluid, saliva, urine for assessing specific biomarkers or water samples, e.g., for testing environmental conditions in bodies of water, wells, reservoirs, etc. In this implementation, the CNTFET devices 10 may be formed as described herein with appropriate receptors bound to the decorated particles for sensing the desired or expected analyte or target of interest. A single microfluidic system 50 could include an array of CNTFET devices 10 wherein individual CNTFET devices 10 or rows or sub blocks of the array of CNTFET devices 10 are bound with receptors for different analytes or targets of interest.

The present embodiments provide for improved controllability compared to existing site specific deposition methods. Using electrodeposition in combination with e-beam lithography, it is possible to precisely control the number, location and size of the Au nanoparticles on the carbon nanotube. After glucose oxidase is specifically bound to the Au nanoparticles, it is possible to tune the sensitivity of glucose detection by varying the parameters mentioned above. Finally ultra-sensitive glucose detection can be achieved when a low amount of Au nanoparticles are deposited onto the carbon nanotubes.

Figure 6:
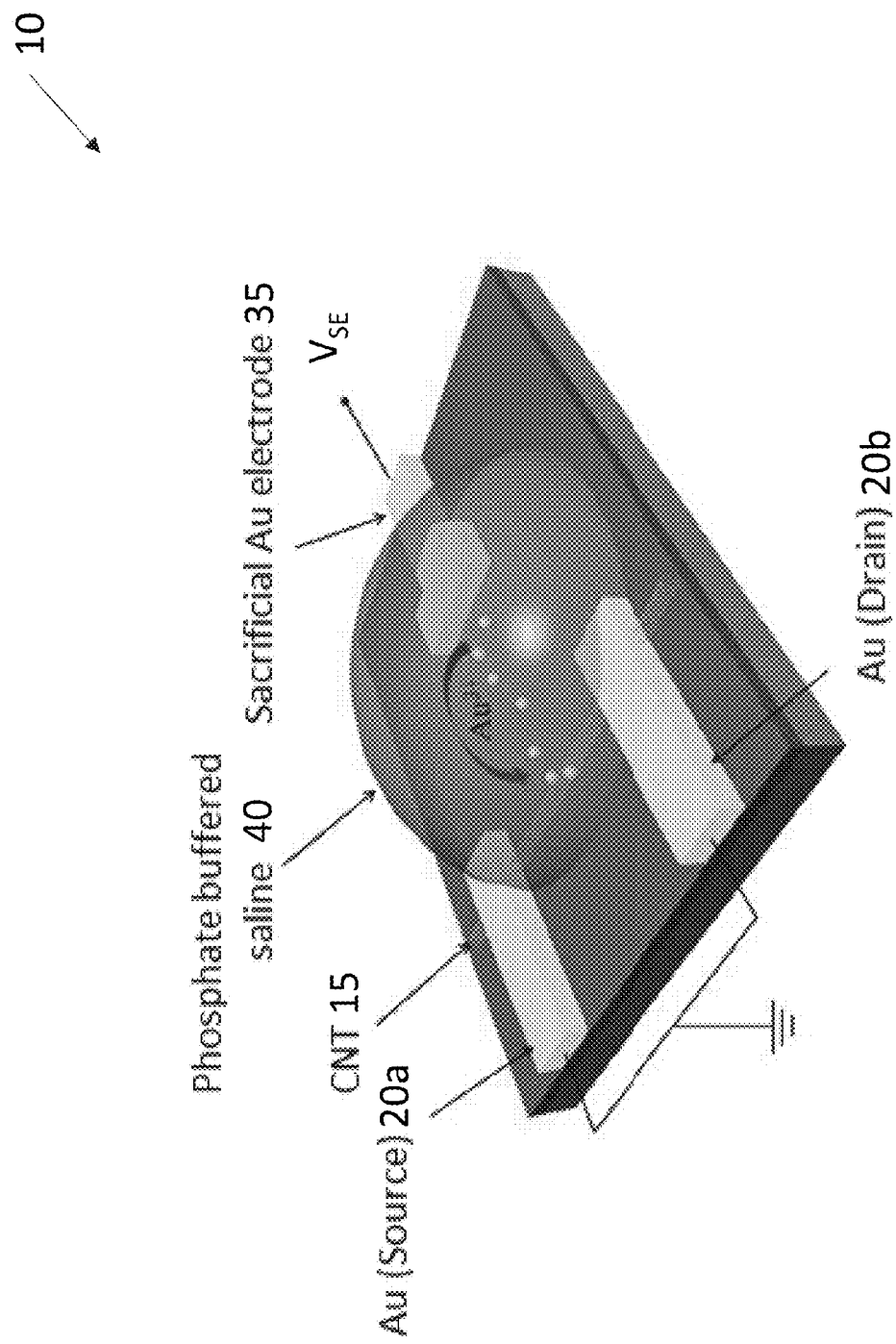
FIG. 6 is a schematic of a pre-Au deposition CNTFET device for Au nanoparticle deposition in accordance with embodiments described herein.

This site-specific nanoparticle deposition method is not limited to Au nanoparticles. It can also be used to deposit other metal nanoparticles such as silver (Ag), palladium (Pd) and platinum (Pt). For single material depositions, the deposition setup would be the same as shown in FIGS. 5 and 6. The only modification would be to change the Au sacrificial electrode to the other metal sacrificial electrode. Through the use of this method, CNTFET devices can be decorated with different metal nanoparticles for different functions. For example palladium can be used to decorate carbon nanotubes toward detection of $H_2$ and $CH_4$ at ambient temperatures and platinum-coated carbon nanotubes can be used to detect low levels of carbon monoxide. When the metal nanoparticle decorated carbon nanotubes are exposed to gas molecules, the adsorbed gas molecules at metal nanoparticle-nanotube junction alter the work function of the metal and therefore change the band alignment, resulting in a change of the electric conductance. The detection of the gas molecule can be realized through the monitoring of the conductance of the carbon nanotubes.

Figure 13:
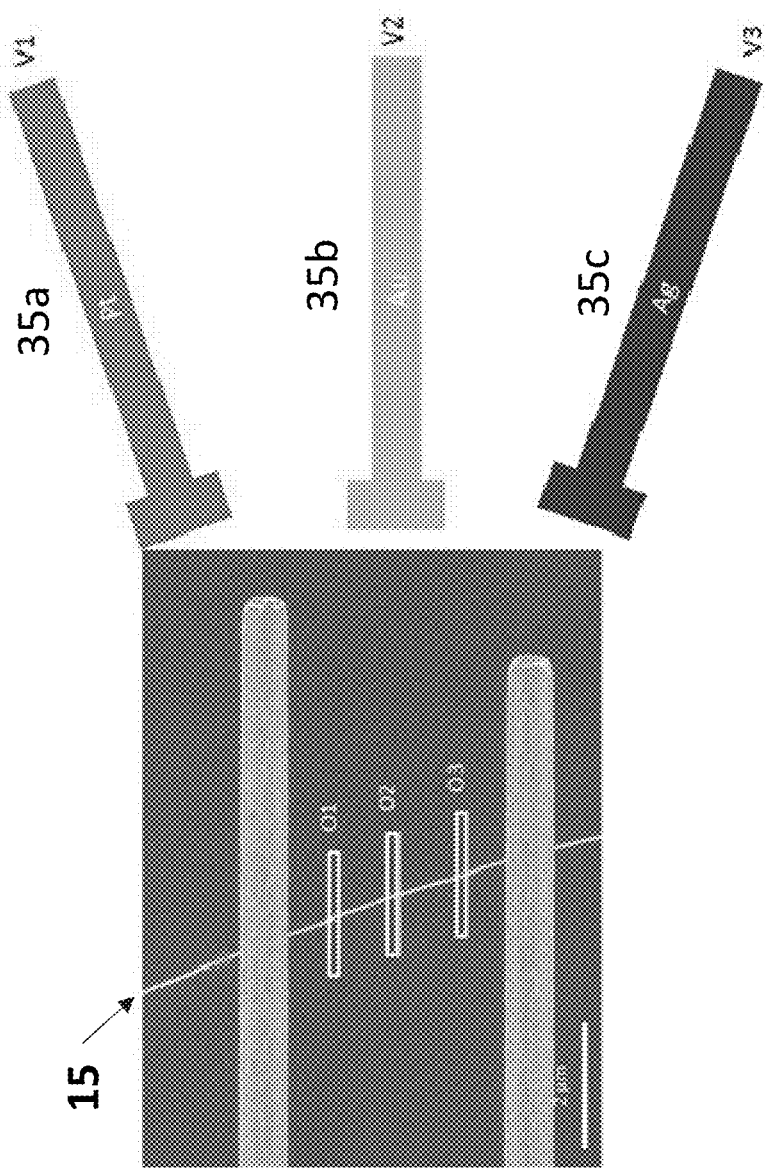
FIG. 13 is a schematic of a pre-deposition CNTFET device for multiple nanoparticle deposition in accordance with embodiments described herein.

Alternatively, referring to FIG. 13, a single CNT 15 may be decorated by nanoparticles comprised of different materials. By way of example, sacrificial electrodes 35*a* (Pt), 35*b* (Au) and 35*c* (Ag) are separately (serially) sacrificed when an appropriate voltage is applied to the sacrificial electrode. Applied voltages V1, V2 and V3 vary in accordance with the material of the sacrificial electrode. Referring to FIG. 13, in a serial exposure process, portion O1 is selectively exposed to Pt nanoparticles when V1 is applied to electrode 35*a*. Next, portion O2 is selectively exposed to Au nanoparticles when V2 is applied to electrode 35*b*. Finally, portion O3 is selectively exposed to Ag nanoparticles when V3 is applied to electrode 35*c*. Portions O1, O2 and O3 may be patterned in accordance with the e-beam lithography process described above and selectively protected when other portions are being decorated. Alternatively, portions O1, O2 and O3 may be patterned as needed.

It should be apparent to one of ordinary skill in the art that other embodiments can be readily contemplated in view of the teachings of the present specification. Such other embodiments, while not specifically disclosed nonetheless fall within the scope and spirit of the present invention. Thus, the present invention should not be construed as being limited to the specific embodiments described above, and is solely defined by the following claims.

We claim:

1. A process for forming a functionalized carbon nanotube field effect transistor (CNTFET) device including site-specific nanoparticle deposition on a carbon nanotube field effect transistor (CNTFET) including one or more carbon nanotubes, a source electrode, a drain electrode, and a sacrificial electrode on a substrate with an interposed dielectric layer, the process comprising:
- passivating the CNTFET with a layer of Poly(methyl methacrylate) (PMMA);
- programming a processor of an electron-beam lithography system with a predetermined removal pattern;
- applying electron-beam lithography using the electron-beam lithography system to the CNTFET to remove portions of the PMMA layer and expose one or more underlying portions of the one or more carbon nanotubes and the sacrificial electrode of the CNTFET in accordance with the programmed predetermined removal pattern;
- applying an amount of an electrolyte solution to the CNTFET, including the exposed one or more underlying portions of the one or more carbon nanotubes and the sacrificial electrode;
- applying a voltage to the sacrificial electrode while grounding the source and drain electrodes; and
- electrodepositing one or more nanoparticles formed from atoms of the sacrificial electrode onto the one or more exposed portions of the one or more carbon nanotubes.

2. The process according to claim 1, further comprising: electrodepositing a single nanoparticle onto each of the one or more exposed portions of the one or more carbon nanotubes.

3. The process according to claim 1, wherein the atoms are gold (Au) atoms and the one or more nanoparticles are gold (Au) nanoparticles.

4. The process according to claim 1, further comprising removing remaining PMMA from the CNTFET after the electrodeposition.

5. The process according to claim 1, further comprising controlling at least one of size and number of electrodeposited nanoparticles by controlling the voltage applied to the sacrificial electrode in combination with the predetermined removal pattern.

6. The process according to claim 1, wherein the programmed predetermined removal pattern instructs the electron-beam lithography system to remove PMMA from the one or more carbon nanotubes to expose a single underlying portion of the one or more carbon nanotubes having a dimension only slightly larger than a predetermined dimension of a single nanoparticle.

7. The process according to claim 1, wherein the programmed predetermined removal pattern instructs the electron-beam lithography system to remove PMMA from the one or more carbon nanotubes to expose multiple individual underlying portions of the one or more carbon nanotubes, each individual underlying portion having a dimension only slightly larger than a predetermined dimension of a single nanoparticle.

8. The process according to claim 4, further comprising depositing a protective passivation layer on the source and drain electrodes.

9. The process according to claim 3, further comprising binding a glucose oxidase molecules (GOx) to the one or more Au nanoparticles using one or more thiol linking molecules.

10. The process according to claim 1, wherein the one or more nanoparticles have a dimension in the range of 10 nanometers to 100 nanometers.

11. A process for forming a functionalized carbon nanotube field effect transistor (CNTFET) device including site-specific nanoparticle deposition on a carbon nanotube field effect transistor (CNTFET) including one or more carbon nanotubes, a source electrode, a drain electrode, and a sacrificial electrode on a substrate with an interposed dielectric layer, the process comprising:
- removing portions of a protective layer covering the one or more carbon nanotubes in accordance with a predetermined removal pattern to expose one or more individual underlying portions of the one or more carbon nanotubes and to expose the sacrificial electrode of the CNTFET, wherein each of the exposed one or more individual underlying portions of the one or more carbon nanotubes has a first predetermined dimension;
- applying an amount of an electrolyte solution to the CNTFET, including the exposed one or more underlying portions of the one or more carbon nanotubes and the sacrificial electrode;
- applying a voltage to the sacrificial electrode while grounding the source and drain electrodes; and
- electrodepositing one or more nanoparticles each having a predetermined second dimension formed from atoms of the sacrificial electrode onto the one or more exposed portions of the one or more carbon nanotubes, wherein the first predetermined dimension is only slightly larger than the second predetermined dimension.

12. The process according to claim 11, wherein the atoms are gold (Au) atoms and the one or more nanoparticles are gold (Au) nanoparticles.

13. The process according to claim 11, further comprising removing remaining protective layer from the CNTFET after the electrodeposition.

14. The process according to claim 11, further comprising controlling at least one of size and number of electrodeposited nanoparticles by controlling the voltage applied to the sacrificial electrode in combination with the predetermined removal pattern.

15. The process according to claim 13, further comprising depositing a protective passivation layer on the source and drain electrodes.

16. The process according to claim 12, further comprising binding a glucose oxidase molecules (GOx) to the one or more Au nanoparticles using one or more thiol linking molecules.

17. The process according to claim 11, wherein the first predetermined dimension and the second predetermined dimension are in the range of 10 nanometers to 100 nanometers.

18. A microfluidic device for assessing the contents of fluid introduced thereto comprising:
- at least one microfluidic channel having multiple functionalized carbon nanotube field effect transistors (CNTFET) formed in accordance with the process of claim 1 and including one or more carbon nanotubes, a source electrode, and a drain electrode formed on a substrate with an interposed dielectric layer;
- a single access point formed in the microfluidic device for introducing the fluid to the at least one microfluidic channel; and
- a single exit point formed in the microfluidic device for removing the fluid from the least one microfluidic channel.

19. The device of claim 18, wherein the fluid is selected from the group consisting of water, blood, interstitial fluid, saliva and urine.

20. The device of claim 18, wherein each of the multiple CNTFETs in the microfluidic channel is functionalized to assess presence of a different analyte in the fluid.

21. A process for forming a functionalized carbon nanotube field effect transistor (CNTFET) device including site-specific nanoparticle deposition on a carbon nanotube field effect transistor (CNTFET) including one or more carbon nanotubes, a source electrode, a drain electrode, and at least a first and second sacrificial electrode on a substrate with an interposed dielectric layer, the process comprising:

removing portions of a protective layer covering the one or more carbon nanotubes in accordance with a first predetermined removal pattern to selectively expose a first individual underlying portion of the one or more carbon nanotubes and to selectively expose the first sacrificial electrode of the CNTFET;

applying an amount of an electrolyte solution to the CNTFET, including the exposed first underlying portion and the exposed first sacrificial electrode;

applying a first voltage to the first sacrificial electrode while grounding the source and drain electrodes;

electrodepositing one or more nanoparticles formed from first atoms of the first sacrificial electrode onto the first exposed underlying portions of the one or more carbon nanotubes;

removing portions of a protective layer covering the one or more carbon nanotubes in accordance with a second predetermined removal pattern to selectively expose a second individual underlying portion of the one or more carbon nanotubes and to selectively expose the second sacrificial electrode of the CNTFET;

applying an amount of an electrolyte solution to the CNTFET, including the exposed second underlying portion and the exposed second sacrificial electrode;

applying a second voltage to the second sacrificial electrode while grounding the source and drain electrodes; and electrodepositing one or more nanoparticles formed from second atoms of the second sacrificial electrode onto the second exposed underlying portions of the one or more carbon nanotubes.

22. The process according to claim 21, wherein the first and second sacrificial electrodes are different and are selected from the group consisting of: gold (Au); silver (Ag), palladium (Pd) and platinum (Pt).

23. The process according to claim 21, further comprising controlling at least one of size and number of electrodeposited nanoparticles by controlling the first voltage applied to the first sacrificial electrode and the second voltage applied to the second sacrificial electrode in combination with the first and second predetermined removal patterns.

* * * * *